United States Patent [19]

Herrmann et al.

[11] Patent Number: 5,329,013

[45] Date of Patent: Jul. 12, 1994

[54] **PROCESS FOR THE PREPARATION OF TRICYCLO-[3.3.1.1³,⁷]DEC-2-YL-[R-(R*,R*)]-3-(1H-INDOL-3-YLMETHYL)-3-METHYL-4,9-DIOXO-7,11-DIPHENYL-10-OXA-2,5,8-TRIAZAUNDECANATE**

[75] Inventors: Wolfgang Herrmann, Freiburg; Klaus Steiner, Waldkirch; Hans-Joachim Witzke, Nimburg, all of Fed. Rep. of Germany

[73] Assignee: Gödecke Aktiengesellschaft, Berlin, Fed. Rep. of Germany

[21] Appl. No.: 966,217

[22] Filed: Oct. 26, 1992

[30] Foreign Application Priority Data

Nov. 14, 1991 [DE] Fed. Rep. of Germany ....... 4137490

[51] Int. Cl.⁵ .................. C07D 209/26; C07C 271/20
[52] U.S. Cl. ...................................... 548/496; 560/169
[58] Field of Search ........................ 548/496; 560/169

[56] References Cited

PUBLICATIONS

Horwell, D. C., et al., *J. Med. Chem.*, 1991; 34:404–14.

*Primary Examiner*—David B. Springer
*Attorney, Agent, or Firm*—Elizabeth M. Anderson

[57] ABSTRACT

The present invention provides a process for the preparation of tricyclo- [3.3.1.1³,⁷]dec-2-yl-[R-(R*,R*)]-3-(1H-indol-3-ylmethyl)-3-methyl-4,9-dioxo-7,11-diphenyl-10-oxa-2,5,8-triazaundecanate, an important compound in the preparation of a new class of cholecystokinin inhibitors, wherein N-[(benzyloxy)carbonyl]-(R)-$\beta$-amino-1-azido-2-phenylethane is hydrogenated, and subsequently, by means of carbon dioxide, the resulting N$^\beta$-[(benzyloxy)-carbonyl]-(R)-$\beta$-amino-2-phenylethylamine carbonate is precipitated out. This is coupled by the carbodiimide process with N-[(2-adamantyloxy)-carbonyl]-$\alpha$-methyl-R-tryptophane.

2 Claims, No Drawings

PROCESS FOR THE PREPARATION OF TRICYCLO-[3.3.1.1³,⁷]DEC-2-YL-[R-(R*,R*)]-3-(1H-INDOL-3-YLMETHYL)-3-METHYL-4,9-DIOXO-7,11-DIPHENYL-10-OXA-2,5,8-TRIAZAUNDECANATE

BACKGROUND OF THE INVENTION

The present invention is a process for the preparation of tricyclo-[3.3.1.1³,⁷]dec-2-yl- [R-(R*,R*)]-3-(1H-indol-3-ylmethyl)-3-methyl-4,9-dioxo-7,11-diphenyl-10-oxa-2,5,8-triazaundecanate of the formula:

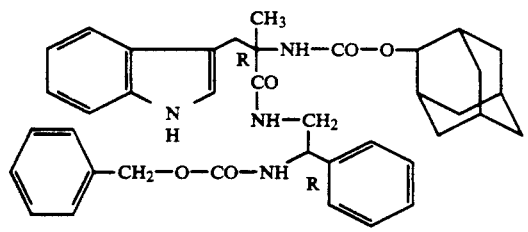

This compound is a key compound in the preparation of a new class of highly selective and orally effective gastrin and CCK-B antagonists (see D. C. Horwell et al, *J. Med. Chem.*, 1991;34:404–14. The compounds, their preparation, methods of using them, and compositions containing them are found in U.S. Ser. No. 07/629,809, filed Dec. 12, 1990 hereby incorporated by reference. The final products are useful as pharmaceutical agents in the treatment of anxiety, appetite disorders, excess gastric acid secretion, gastrointestinal ulcers, psychoses reaction caused by drug or alcohol withdrawal, cocaine, benzodiazepine, or nicotine withdrawal to potentiate the effects of morphine, pain, and depression for cognition.

It is an object of the present invention to provide an economical process, which can be carried out on a technical scale, for the preparation of this compound with a high degree of purity.

DETAILED DESCRIPTION

In Scheme 1 below, the carbodiimide method uses 1-hydroxybenztriazole hydrate as catalyst, starting from an optically-active, mono-protected diamine of Formula (II), with the also optically-active R-α-methyltryptophane derivative of Formula (III). The mono-protected diamine (II) is prepared starting from R-(−)-α-phenylglycinol via N-[(benzyloxy)carbonyl]-(R)-β-amino-2-phenylethanol (IV) and N-[(benzyloxy)carbonyl]-O-(toluene-4-sulphonyl)-(R)-β-amino-2-phenylethanol (V).The last-mentioned tosyl compound (V) is reacted with sodium azide in dimethylformamide to give N-[(benzyloxy)-carbonyl]-(R)-β-amino-1-azido-2-phenylethane (VI) which is subsequently hydrogenated to give the mono-protected diamine $N^B$-[(benzyloxy)-carbonyl]-(R)-β-amino-2-phenylethylamine (II).

Scheme 1

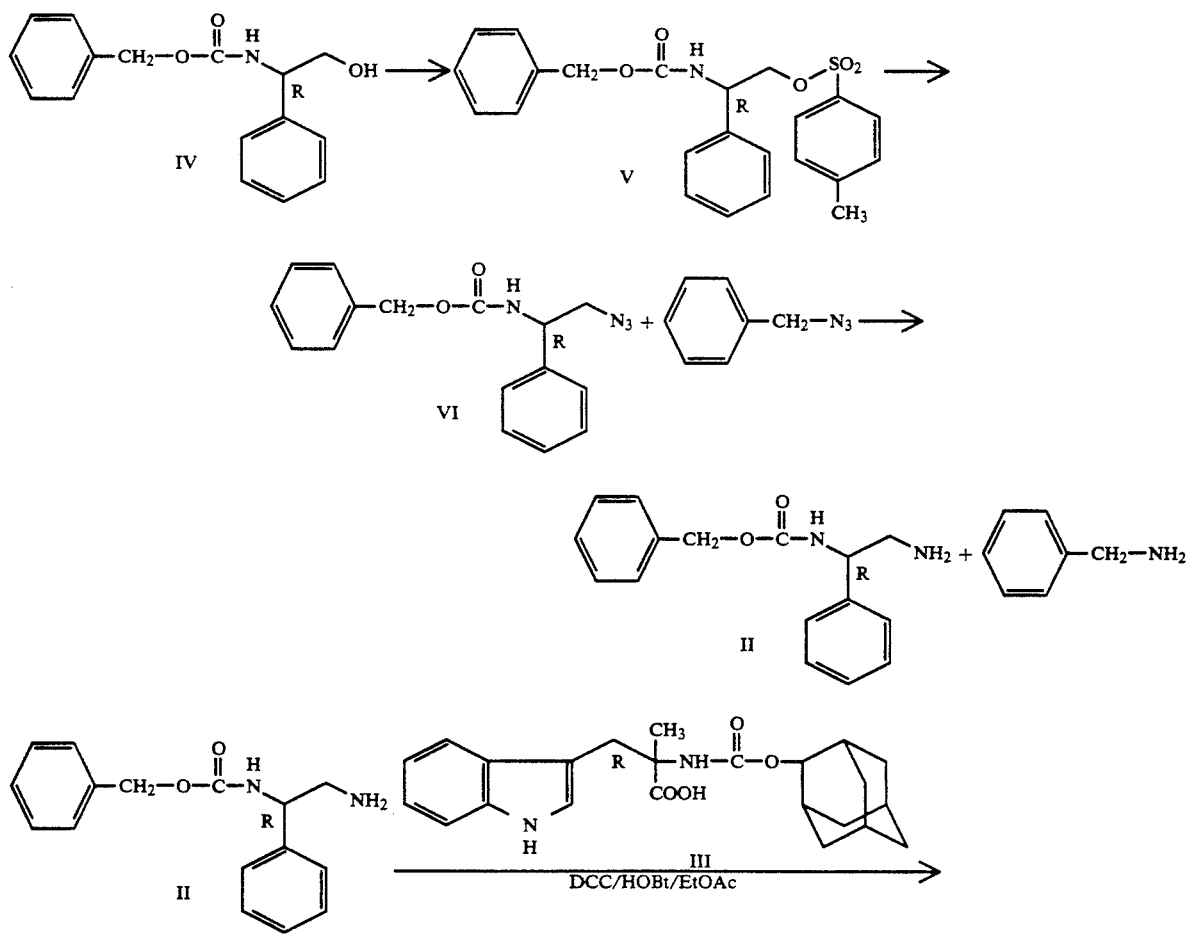

-continued
Scheme 1

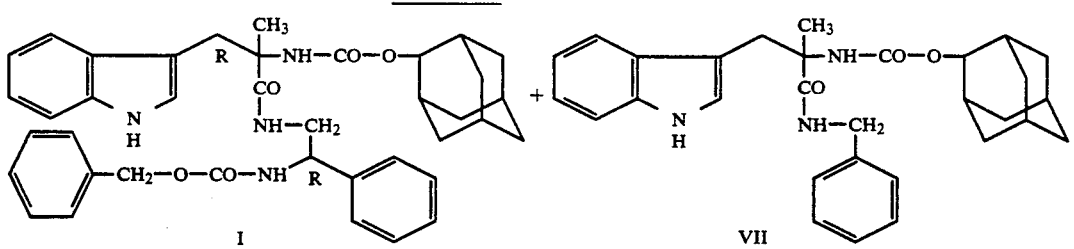

The process of the instant invention is preferred over the known process (see D. C. Horwell et al, *J. Med. Chem.*, 1991;34:404-14), as the reaction of the tosyl compound of Formula (V) with sodium azide, a crude azide results which, besides the desired compound of Formula (II), also contains up to 5% of benzylazide which cannot be removed at this stage because of the potential instability of azides. Consequently, in the subsequent hydrogenation of the azide mixture, a crude amine mixture results which, besides the desired amine of Formula (II), also contains, inter alia, benzylamine. This benzylamine cannot be separated off without great effort and, in the subsequent coupling with the R-β-methyltryptophane derivative of Formula (III), reacts analogously to the amine (II). The resulting impurity of Formula (VII) can only be separated by a laborious column chromatographic purification, which must often be carried out several times. Since the N-β-[(benzyloxy)-carbonyl]-(R)-β-amino-2-phenylethylamine of Formula (II) is obtained as an oily crude mixture, the precise amount of the desired product can only be ascertained with difficulty. The subsequent coupling reaction uses it in an approximately 45% excess. The reaction mixture obtained must be purified by an extremely laborious and time-consuming column chromatographic separation in order to obtain an end product (I) which is sufficiently pure for further reactions. Furthermore, N-β-[(benzyloxy)-carbonyl]-(R)-β-amino-2-phenylethylamine (II) proves to be storage-unstable since this amine absorbs carbon dioxide from the air and is thereby partly converted into a carbonate which is insoluble in the solvents used for the coupling.

Surprisingly, we have now found that the amine (II) forms a stable, sparingly soluble, nonhygroscopic stoichiometric salt (VIII) with carbonic acid when the crude azide, without any further purification, is hydrogenated in ethyl acetate in the presence of a catalyst, for example, Raney nickel. A small amount of alcohol is added to the clearly filtered solution and subsequently gaseous carbon dioxide is passed in or solid carbon dioxide is added. See Scheme 2 below.

Scheme 2

The carbonate (VIII) thereby precipitating out selectively and almost quantitatively with an absolute purity of >98%, benzylamine remaining behind in the mother liquor as impurity.

Furthermore, we have, surprisingly, found that the carbonate salt of the amine (VIII) can be directly reacted in stoichiometric amount, i.e., without liberation of the amine (II), with the R-α-methyltryptophane derivative (III) to give the title Compound (I) in Scheme 3 below.

Scheme 3

In the above process, the title Compound (I) is obtained in almost quantitative yield and, without column chromatographic purification, with a purity of about 98% and can be used directly for the further synthesis of various active materials.

The following Examples are given for the purpose of illustrating the present invention.

EXAMPLE 1

N$^\beta$-[(Benzyloxy)-carbonyl]-(R)-$\beta$-amino-2-phenylethaneamine carbonate 22.7 g N-[(Benzyloxy)-carbonyl]-(R)-$\beta$-amino-1-azido-2-phenylethane were dissolved in 300 mL ethyl acetate and hydrogenated for 15-hours at 25° C. and at a pressure of 80 ats in the presence of 7.3 g Raney nickel (B 113 W, Degussa). The hydrogenation solution was filtered clear and subsequently mixed with 90 mL ethanol. Gaseous carbon dioxide was passed into this solution, causing a white product to precipitate out. The filter cake was washed with a little ethyl acetate/ethanol (10:3 v/v). The product was dried at 40° C. in a circulating air cabinet. The yield of N$^\beta$-[(benzyloxy)-carbonyl]-(R)-$\beta$-amino-2-phenylethylamine carbonate was 18.5 g (79.5% of theory); mp 136.3° C.; $[\alpha]_D = -34.1°$ C. (c=1/methanol).

EXAMPLE 2

Tricyclo-[3.3.1.1$^{3,7}$]dec-2-yl-[R-(R*,R*)]-3-(1H-indol-3-ylmethyl)-3-methyl-4,9-dioxo-7,11-diphenyl-10-oxa-2,5,8-triazaundecanate 4.08 g N-[(2-Adamantyloxy)-carbonyl]-$\alpha$-ethyl-R-tryptophane were dissolved in 25 mL ethyl acetate and mixed at 20° C. with 1.53 g 1-hydroxy-1H-benztriazole hydrate and 2.06 g dicyclohexylcarbodiimide. After stirring for 2 hours at 20° C., precipitated dicylohexylurea (2.12 g=94.6% of theory) was filtered off. 3.01 g N-$^B$-[(benzyloxy)-carbonyl]-(R)-$\beta$-amino-2 -phenylethylamine carbonate was added, while stirring, to the clear filtrate over the course of about 15 minutes, the carbonate going into solution with the formation of carbon dioxide. The reaction mixture was stirred for 16 hours. After filtering clear, 25 mL ethyl acetate were added thereto. The solution was washed 3 times with 150 mL 5% citric acid solution, 2 times with 150 mL 5% sodium hydrogen carbonate solution, and subsequently with 25 mL water. If an emulsion is formed, it can be broken by the addition of sodium chloride. The organic phase was dried over anhydrous sodium sulphate and filtered. After evaporation on a rotary evaporator, a foamy product remained behind (6.05 g=93% of theory; HPLC: 98.89 relative %) .

We claim:

1. Process for the preparation of tricyclo [3.3.1.1$^{3,7}$]dec-2-yl-[R-(R*,R*)]-3-(1H-indol-3-ylmethyl)-3-methyl-4,9-dioxo-7,11-diphenyl-10-oxa-2,5,8-triazaundecanate, which consists of hydrogenation of N-[(benzyloxy)-carbonyl]-(R)-$\beta$-amino-1-azido-2-phenylethane of formula

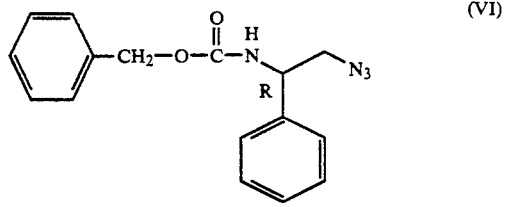

in ethyl acetate in the presence of a Raney nickel catalyst and reacting VI with gaseous or solid carbon dioxide to form N$^\beta$-[(benzyloxy)-carbonyl]-(R)-$\beta$-amino-2-phenylethylamine carbonate of formula

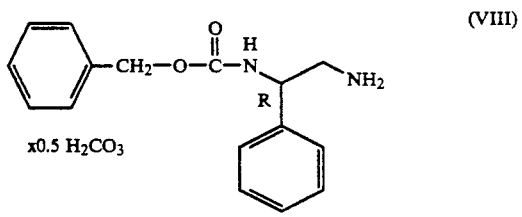

which precipitates out of solution VIII and is reacted directly in stoichiometric amount with N-[(2-adamantyloxy)carbonyl]-$\alpha$-methyl-R-tryptophane of the formula

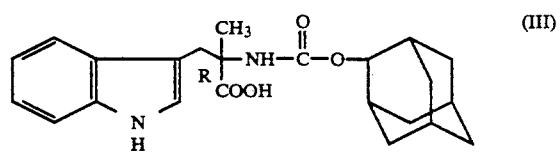

dissolved in ethyl acetate and mixed at about 20° C. with 1hydroxy-1H-benztriazole hydrate and dicyclohexylcarboximide to form the final product

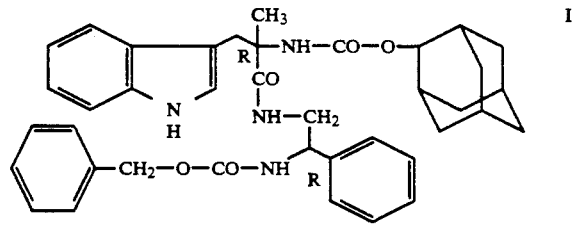

and converting, if desired, to a pharmaceutically acceptable salt.

2. A compound named N$^\beta$-[(benzyloxy)-carbonyl]-(R)-$\beta$-amino-2-phenylethylamine carbonate.

* * * * *